US012635882B2

(12) United States Patent
Lee et al.

(10) Patent No.: US 12,635,882 B2
(45) Date of Patent: May 26, 2026

(54) CALIBRATION CRADLE FOR THREE-DIMENSIONAL SCANNER AND CONTROL METHOD FOR SAME

(71) Applicant: MEDIT CORP., Seoul (KR)

(72) Inventors: Dong Hoon Lee, Seoul (KR); Myoung Woo Song, Seoul (KR); Young Seok Jeong, Seoul (KR)

(73) Assignee: MEDIT CORP., Seoul (KR)

( * ) Notice: Subject to any disclaimer, the term of this patent is extended or adjusted under 35 U.S.C. 154(b) by 262 days.

(21) Appl. No.: 18/277,311

(22) PCT Filed: Feb. 15, 2022

(86) PCT No.: PCT/KR2022/002206
§ 371 (c)(1),
(2) Date: Aug. 15, 2023

(87) PCT Pub. No.: WO2022/177261
PCT Pub. Date: Aug. 25, 2022

(65) Prior Publication Data
US 2024/0138680 A1     May 2, 2024

(30) Foreign Application Priority Data
Feb. 16, 2021    (KR) ........................ 10-2021-0020464

(51) Int. Cl.
*A61B 5/00*                (2006.01)
(52) U.S. Cl.
CPC .......... *A61B 5/0062* (2013.01); *A61B 5/0088* (2013.01); *A61B 2560/0228* (2013.01); *A61B 2560/0456* (2013.01)

(58) Field of Classification Search
CPC ................ A61B 5/0062; A61B 5/0088; A61B 2560/0228; A61B 2560/0456; A61B 1/00;
(Continued)

(56) References Cited

U.S. PATENT DOCUMENTS

2003/0068079 A1    4/2003  Park
2006/0102833 A1    5/2006  Eiff et al.
(Continued)

FOREIGN PATENT DOCUMENTS

CN         108269287 A      7/2018
CN         110132165 A      8/2019
(Continued)

OTHER PUBLICATIONS

International Stage Entry of PCT/KR2022/002206 dated May 30, 2022 [PCT/ISA/210].
(Continued)

*Primary Examiner* — Tony Ko
(74) *Attorney, Agent, or Firm* — Sughrue Mion, PLLC

(57) ABSTRACT
The present invention relates to a calibration cradle for a three-dimensional scanner. Particularly, the calibration cradle comprises: a cradle body into which a front end portion of a three-dimensional scanner is inserted and seated; a calibration pattern plate (hereinafter, abbreviated as "pattern plate") which is disposed inside the cradle body to correct the scanning of the three-dimensional scanner; and a pattern movement part which automatically axially rotates and axially reciprocates the pattern plate in the cradle body when the three-dimensional scanner is coupled to the cradle body, whereby the present invention provides an advantage of improving the convenience and reliability of performing calibration.

20 Claims, 14 Drawing Sheets

(58) Field of Classification Search
CPC ................. A61B 1/24; A61B 1/00057; A61B
2560/0223; A61C 9/00; A61C 9/0053
See application file for complete search history.

(56) References Cited

U.S. PATENT DOCUMENTS

| | | |
|---|---|---|
| 2015/0288952 A1 | 10/2015 | Popilka et al. |
| 2016/0191901 A1 | 6/2016 | Stegall et al. |
| 2018/0333232 A1* | 11/2018 | Lee .......................... A61B 1/24 |
| 2021/0045637 A1 | 2/2021 | Chang et al. |

FOREIGN PATENT DOCUMENTS

| | | |
|---|---|---|
| CN | 112074228 A | 12/2020 |
| KR | 10-2002-0028133 A | 4/2002 |
| KR | 10-2015-0082438 A | 7/2015 |
| KR | 10-1941001 B1 | 1/2019 |
| KR | 10-2129383 B1 | 7/2020 |

OTHER PUBLICATIONS

Korean Office Action dated Oct. 17, 2022 in Korean Application No. 10-2021-0020464.
Korean Final Office Action issued Apr. 21, 2023 in Korean Application No. 10-2021-0020464.
Communication dated Jan. 1, 2026 in Chinese Application No. 202280015212.X.

* cited by examiner

"C"          "Object to be measured"

110

255

1

"D"

1

CALIBRATION CRADLE FOR THREE-DIMENSIONAL SCANNER AND CONTROL METHOD FOR SAME

CROSS REFERENCE TO RELATED APPLICATIONS

This application is a National Stage of International Application No. PCT/KR2022/002206 filed Feb. 15, 2022, claiming priority on Korean Patent Application No. 10-2021-0020464 filed Feb. 16, 2021, the entire disclosures of which are incorporated herein by reference.

TECHNICAL FIELD

The present disclosure relates to a calibration cradle for a three-dimensional scanner and a control method therefor and, more specifically, to a calibration cradle for a three-dimensional scanner capable of improving calibration accuracy of a three-dimensional scanner and improving user convenience during calibration and a control method therefor.

BACKGROUND

A three-dimensional scanner is a type of scanner that acquires multiple optical images of a target object and uses the optical images to produce three-dimensional model data of the target object. A handheld scanner refers to a device configured to acquire a series of optical images of parts of a human body, particularly structures within the oral cavity such as teeth and gums, among the various types of three-dimensional scanners.

The handheld scanner may be provided so that a part of the handheld scanner (for example, a probe tip or a tip case having a reflection mirror) may be replaced for sanitary purposes.

In order to acquire accurate three-dimensional model data, an error correction work, that is, calibration, for a three-dimensional scanner is frequently required. For this reason, common to provide a three-dimensional scanner with a calibration tool as a separate accessory.

However, in the case of a conventional handheld scanner, as described above, an optical path of the scanner including a replaceable probe tip (or a tip case) is accommodated inside an accommodation unit formed in a calibration tool to perform calibration, and thus a reversal phenomenon occurs by a reflection mirror provided inside the probe tip (or tip case), thereby causing a problem of decreasing calibration accuracy. In addition, there is a problem of degrading calibration accuracy even when a foreign substance such as fog or water is present in the reflection mirror of the probe tip (or tip case).

In addition, a user has to manually operate a necessarily provided pattern plate at various distances and angles during calibration, and thus it is difficult to guarantee calibration accuracy.

SUMMARY

The present disclosure has been made to solve the above-described technical problem, and an aspect of the disclosure is to provide a calibration cradle for a three-dimensional scanner and a control method therefor, wherein the three-dimensional scanner is inserted and seated in the calibration cradle while a tip case including an optical member is removed for more accurate calibration of the three-dimensional scanner.

In addition, another aspect of the present disclosure is to provide a calibration cradle for a three-dimensional scanner and a control method therefor, wherein a pattern plate is automatically moved when the three-dimensional scanner is inserted and seated in order to perform more accurate calibration of the three-dimensional scanner and improve user convenience.

The technical problems of the present disclosure are not limited to the above-mentioned problems, and other technical problems not mentioned will be clearly understood by those skilled in the art from the description below.

A calibration cradle for a three-dimensional scanner according to an embodiment of the present disclosure may include a cradle body into which at least a part of the three-dimensional scanner including a camera is inserted, a pattern plate disposed inside the cradle body to face the camera to scanning-calibrate the three-dimensional scanner, and a pattern moving unit configured to automatically move the pattern plate by at least one of axial rotation movement or axial movement when the three-dimensional scanner is coupled to the cradle body, wherein the axial direction of the axial rotation movement and the axial movement is a longitudinal direction of the three-dimensional scanner.

The axis may coincide with or be parallel to an optical axis of light emitted from the three-dimensional scanner to the pattern plate.

In addition, the pattern moving unit may causes the pattern plate to make axial rotation movement and axial movement at the same time, and while the pattern plate moves, the angle between the pattern plate and the optical axis of light emitted from the three-dimensional scanner to the pattern plate may be maintained.

In addition, a scanner insertion hole into which the three-dimensional scanner is inserted may be formed in the cradle body, and the scanner insertion hole may be configured to be at a height at which the bottom of the three-dimensional scanner inserted horizontally and the bottom of the cradle body are coplanar.

In addition, a scanner insertion hole into which the three-dimensional scanner is inserted may be formed through the cradle body, and the scanner insertion hole may have a size such that external light is blocked from being introduced into the cradle body when the three-dimensional scanner has been inserted into the scanner insertion hole.

In addition, the pattern moving unit may be electrically operated by an internal power source charged wirelessly or by wire.

In addition, at least one of a mounting sensor configured to detect insertion and seating of the three-dimensional scanner or a scanning position detection unit configured to detect the position of the pattern plate may be provided in the cradle body.

In addition, an illuminance sensor configured to detect light may be provided inside the cradle body, and the illuminance sensor may detect light emitted from the three-dimensional scanner.

In addition, the pattern moving unit may include a driving motor electrically operated and having a rotary shaft, a fixing block fixed inside the cradle body and having a horizontally opened moving guide hole formed therein, and a mounting block having the pattern plate coupled thereto and disposed in the moving guide hole inside the fixing block, wherein the axial direction of the axial rotation movement and the axial movement is an axial direction of the rotary shaft.

In addition the pattern moving unit may further include a transmission block disposed between the driving motor and the mounting block to transmit rotational force of the driving motor to the mounting block, and the transmission block may include a coupling end coupled to the rotary shaft of the driving motor and a rotation blade provided at the coupling end and inserted into a rotation interference hole formed in the mounting block to cause rotation interference.

In addition, the rotation interference hole formed in the mounting block may be formed in a shape which interferes in the rotational direction of the rotation blade and does not interfere in the horizontal direction of the rotation blade.

In addition, the rotation interference hole may be formed such that a depth formed in a horizontal direction from the front end of the rotation blade is at least greater than or equal to a horizontally movable distance of the mounting block.

In addition, the transmission block may receive the rotational driving force of the driving motor via a transmission belt wound around a driving belt pulley provided on the rotary shaft of the driving motor and a driven belt pulley disposed parallel to the rotary shaft of the driving motor.

In addition, the pattern moving unit may further include a moving block provided to interlock with the mounting block and configured to move the mounting block by at least one of rotational movement or linear movement by interference with the fixing block.

In addition, the moving block may move within the moving guide hole, and a rotation guide groove in which a guide member is engaged may be formed on an outer circumferential surface of the moving block or an inner circumferential surface of the fixed block.

In addition, the three-dimensional scanner may include a light projector for emitting light, and light emitted from the light projector may be irradiated directly to the pattern plate without going through another element.

In addition, when the pattern plate is moved at least once, the camera may be operated at least once.

In addition, when the three-dimensional scanner is inserted into the cradle body while the tip case provided in the three-dimensional scanner is removed, the initial position of the pattern plate for performing calibration may be configured differently according to the distance between the camera and the optical member in the tip case.

An embodiment of a control method for a calibration cradle for a three-dimensional scanner of the present disclosure may include a scanner detection operation of detecting the insertion of a three-dimensional scanner into a cradle body, a light detection operation of detecting light emitted by an operation of the three-dimensional scanner, and a calibration performing operation of performing calibration by operating a pattern plate which is linearly moved while rotating with reference to the optical axis inside the cradle body when light is detected by the light detection operation, wherein during the calibration performing operation, the position information of the pattern plate is provided to a controller via a scanning position detection unit provided inside the cradle body.

In the calibration performing operation, when light is detected by the light detection operation after the three-dimensional scanner is inserted, the pattern plate may be restored to an initial position for performing the calibration.

According to a calibration cradle for a three-dimensional scanner and a control method therefor according to an embodiment of the present disclosure, various effects may be achieved as follows.

First, by removing a tip case from the three-dimensional scanner and then performing calibration via the calibration cradle, it is possible to prevent deterioration in calibration accuracy due to foreign matter and an optical member.

Second, it is possible to improve calibration reliability by configuring the pattern plate to be rotated and linearly reciprocated while maintaining the corresponding optical axis path between the optical member of the three-dimensional scanner and an object to be measured.

Third, when the three-dimensional scanner is inserted and seated in the cradle body, the pattern plate may be automatically linearly reciprocated and/or rotated, thereby improving user convenience.

Fourth, calibration may be completed using the data of multiple points acquired via a single process from an initial position to a completion position of the pattern plate provided inside the cradle body, thereby greatly reducing the time required for a calibration process.

BRIEF DESCRIPTION OF DRAWINGS

FIG. 3 is a use state diagram of an embodiment of a calibration cradle for a three-dimensional scanner according to the present disclosure;

FIG. 4A and FIG. 4B are perspective views in one direction and in another direction of a calibration cradle for a three-dimensional scanner according to the present disclosure, respectively, in a state in which the three-dimensional scanner is disassembled from the configuration of FIG. 3;

FIG. 5 and FIG. 6 are exploded perspective views of FIG. 4A and FIG. 4B, respectively;

FIG. 7 is a projected perspective view showing the inside of the configuration of FIG. 3 in a state in which the cradle body is removed;

<Description of reference numerals>

Figure 1:
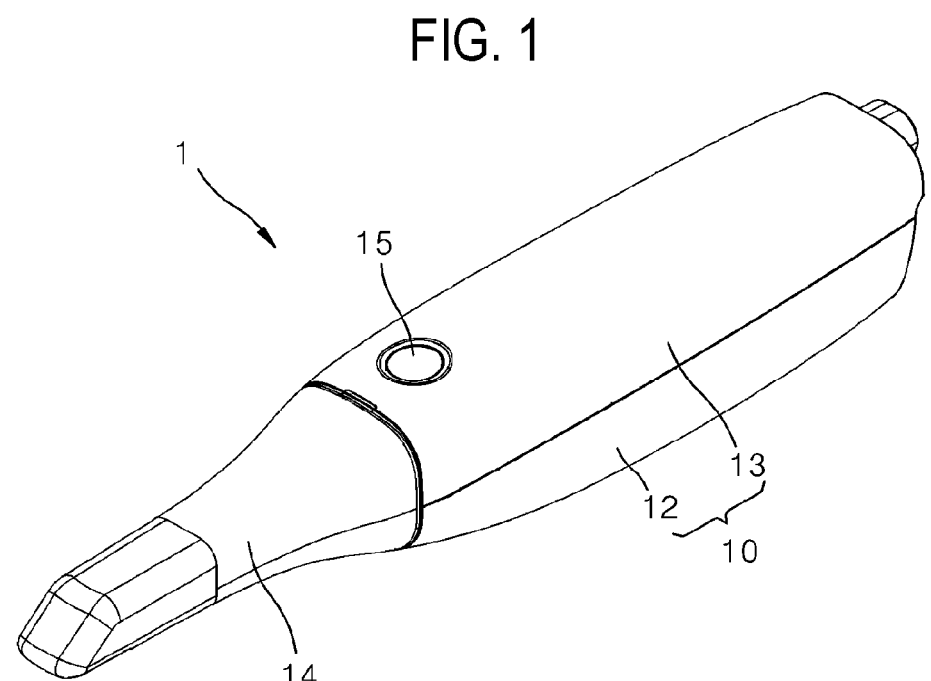
FIG. 1 is a perspective view showing an example of a three-dimensional scanner applied to a calibration cradle for a three-dimensional scanner according to the present disclosure.

| | |
|---|---|
| 1: Three-dimensional scanner | 18: Connection block |
| 100: Calibration cradle | 110: Cradle body |
| 111: Scanner insertion hole | 150: Main printed circuit board |
| 160: Display PCB | 169: Illuminance sensor |
| 170: Scanning position detection unit | 180: Motor PCB |
| 190: Mounting sensor | 200: Pattern moving unit |
| 210: Driving motor | 211: Rotary shaft |
| 220: Center block | 225: Rotary bearing |
| 230: Fixing block | 235: Guide member |
| 240: Transmission block | 241: Coupling end |
| 245: Rotation blade | 250: Mounting block |
| 255: Pattern plate | 260: Moving block |

DETAILED DESCRIPTION

Hereinafter, a calibration cradle for a three-dimensional scanner and a control method therefor according to embodiments of the present disclosure will be described in detail with reference to the accompanying drawings.

In assigning reference numerals to the elements of each drawing, it should be noted that the same elements have the same numerals as much as possible even if the elements are displayed on different drawings. In addition, in describing an embodiment of the present disclosure, if it is determined that a detailed description of a related known configuration or function hinders understanding of the embodiment of the present disclosure, the detailed description thereof will be omitted.

In describing elements of an embodiment of the present disclosure, terms such as first, second, A, B, (a), and (b) may be used. These terms are only used to distinguish the element from other elements, and the nature, sequence, or order of the corresponding element is not limited by the term. In addition, unless defined otherwise, all terms used herein, including technical or scientific terms, have the same meaning as commonly understood by a person skilled in the art to which the present disclosure belongs. Terms such as those defined in commonly used dictionaries should be interpreted as having a meaning which is the same as the meaning in the context of the related art, and unless explicitly defined in this application, the terms should not be interpreted in an ideal or excessively formal meaning.

Figure 2:
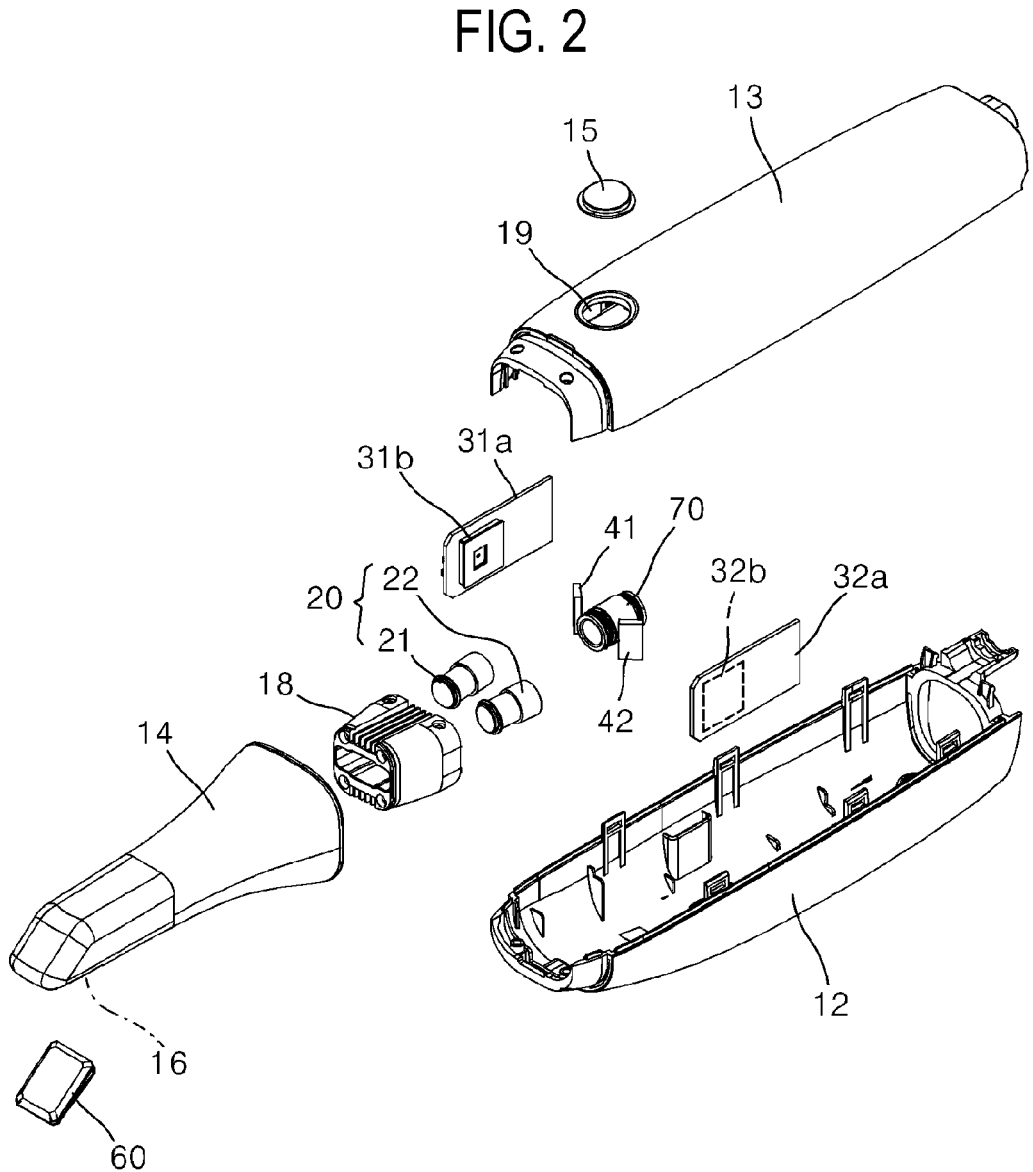
FIG. 2 is an exploded perspective view of the three-dimensional scanner of FIG. 1.

FIG. 1 is a perspective view showing an example of a three-dimensional scanner applied to a calibration cradle for a three-dimensional scanner according to the present disclosure, and FIG. 2 is an exploded perspective view of the three-dimensional scanner of FIG. 1.

First, an example of a three-dimensional scanner 1 which is an object to be applied to a calibration cradle 100 for a three-dimensional scanner according to the present disclosure will be described in detail via referenced drawings as follows.

The three-dimensional scanner 1 applied to the calibration cradle for a three-dimensional scanner according to an embodiment of the present disclosure may include a body case 10 and a tip case 14 capable of being coupled to the body case 10, as referenced in FIG. 1 and FIG. 2.

A camera 20 may be disposed inside the body case 10. The tip case 14 may include an opening portion 16 opened so that an image is introduced into the inside in the form of light via one end of the opening. The opening portion 16 may be an entrance through which external light is introduced into the inside of the tip case 14. Light incident through the opening portion 16 may be transmitted through the camera 20. The light transmitted through the camera 20 may capture an image via imaging sensors 31b and 32b provided on imaging boards 31a and 32a to be described later.

Although not specifically shown, the camera 20 may include at least two transmission lenses capable of adjusting the focus of an image.

To this end, an example of the three-dimensional scanner 1 according to the present disclosure may further include the imaging boards 31a and 32a having the imaging sensors 31b and 32b imaging the light transmitted through the camera 20, respectively. In addition, an example of the three-dimensional scanner 1 according to the present disclosure, although not shown in the drawing, may further include a camera control board on which electric components for controlling the operation of the camera 20 are mounted and a scanning control board on which electric components for processing scanned images are mounted.

As referenced in FIG. 1 and FIG. 2, the body case 10 may serve to provide a predetermined space to allow a plurality of electric components such as the camera 20, the imaging boards 31a and 32a, the camera control board (not shown), and the scanning control board (not shown) to be mounted therein.

More specifically, as referenced in FIG. 2, the body case 10 may include a lower case 12 in which a predetermined space in which the plurality of electric components are embedded is formed, and an upper case 13 provided at an upper side of the lower case 12 and detachably coupled to the lower case 12 to cover the above elements. Light incident to the inside of the body case 10 through the opening portion 16 may indicate incident light, and light emitted from the inside of the body case 10 through the opening portion 16 may be emitted light, and may indicate irradiation light emitted from a light projector 70 to be described later.

The internal structure of the tip case 14 may be formed as a light guide structure through which the incident light and the outgoing light are easily emitted to the inside and outside of the body case 10. In addition, the opening portion 16 may be formed to be open in one direction orthogonal to the longitudinal direction of the tip case 14, and an optical member 60 to be described later may be disposed in the opening portion 16.

A connection block 18 may be further provided between a front end of the body case 10 and a rear end of the tip case 14, as referenced in FIG. 2. The connection block 18 may be inserted into and placed in a cradle body to be described later, and may thus perform a role of stably performing calibration.

As shown in FIG. 2, an embodiment of the three-dimensional scanner 1 according to the present disclosure may further include a light projector 70 disposed inside the body case 10 and emitting outgoing light through the opening portion 16 formed at one end of the tip case 14.

The outgoing light emitted from the light projector 70 may be refracted via the optical member 60 of the tip case 14 and emitted to an object to be measured and, at the same time, the outgoing light reflected from the object to be measured may be incident via the optical member 60 of the tip case 14 in the form of incident light and may pass through the camera 20 provided inside the body case 10 to be image-processed by the imaging sensors 31b and 32b of the imaging boards 31a and 32a. The optical member 60 provided in the tip case 14 may be provided with either a prism or a mirror.

Figures 3, 4A:
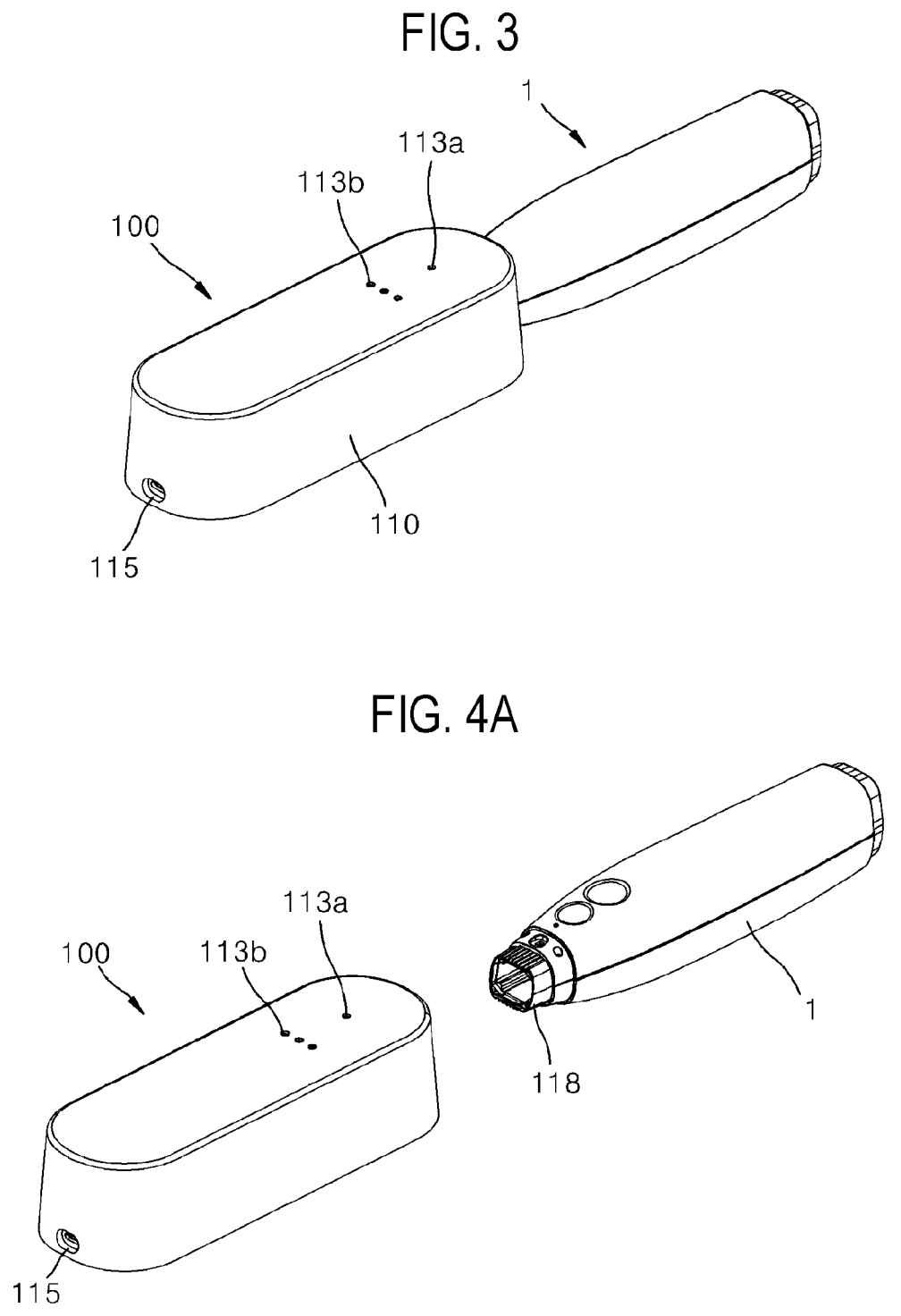
Figure 4B:
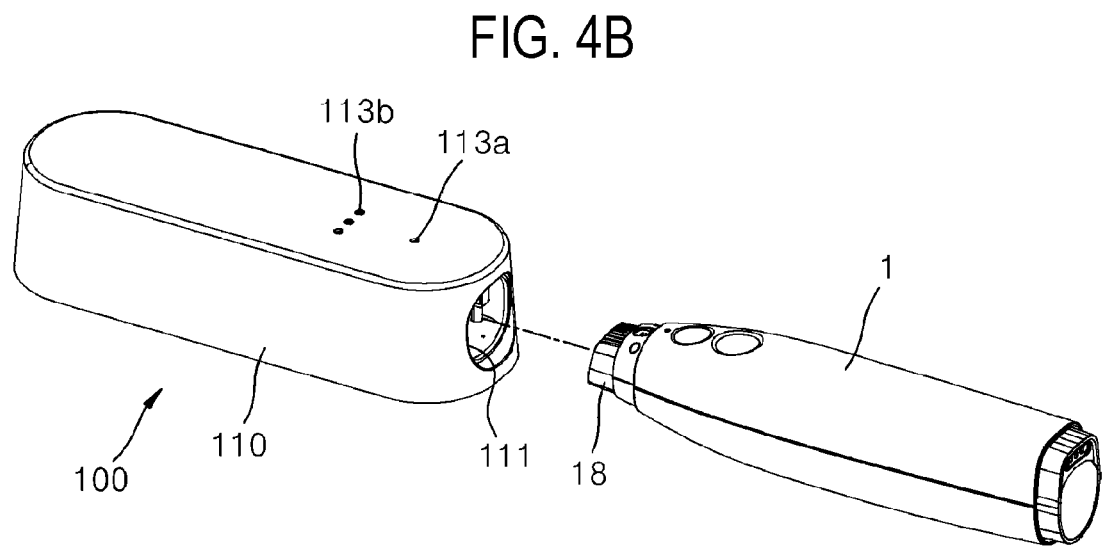
Figure 5:
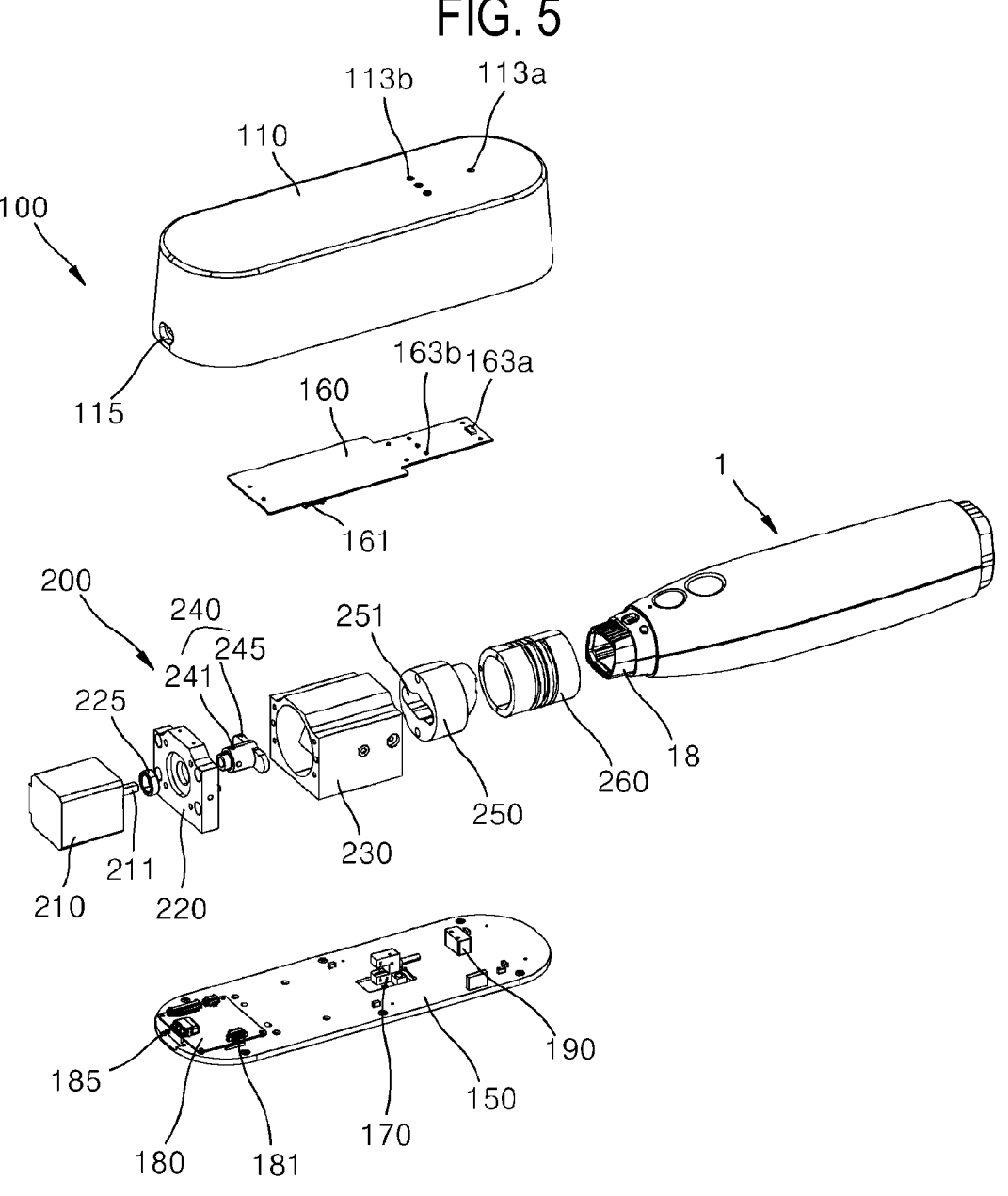
Figure 6:
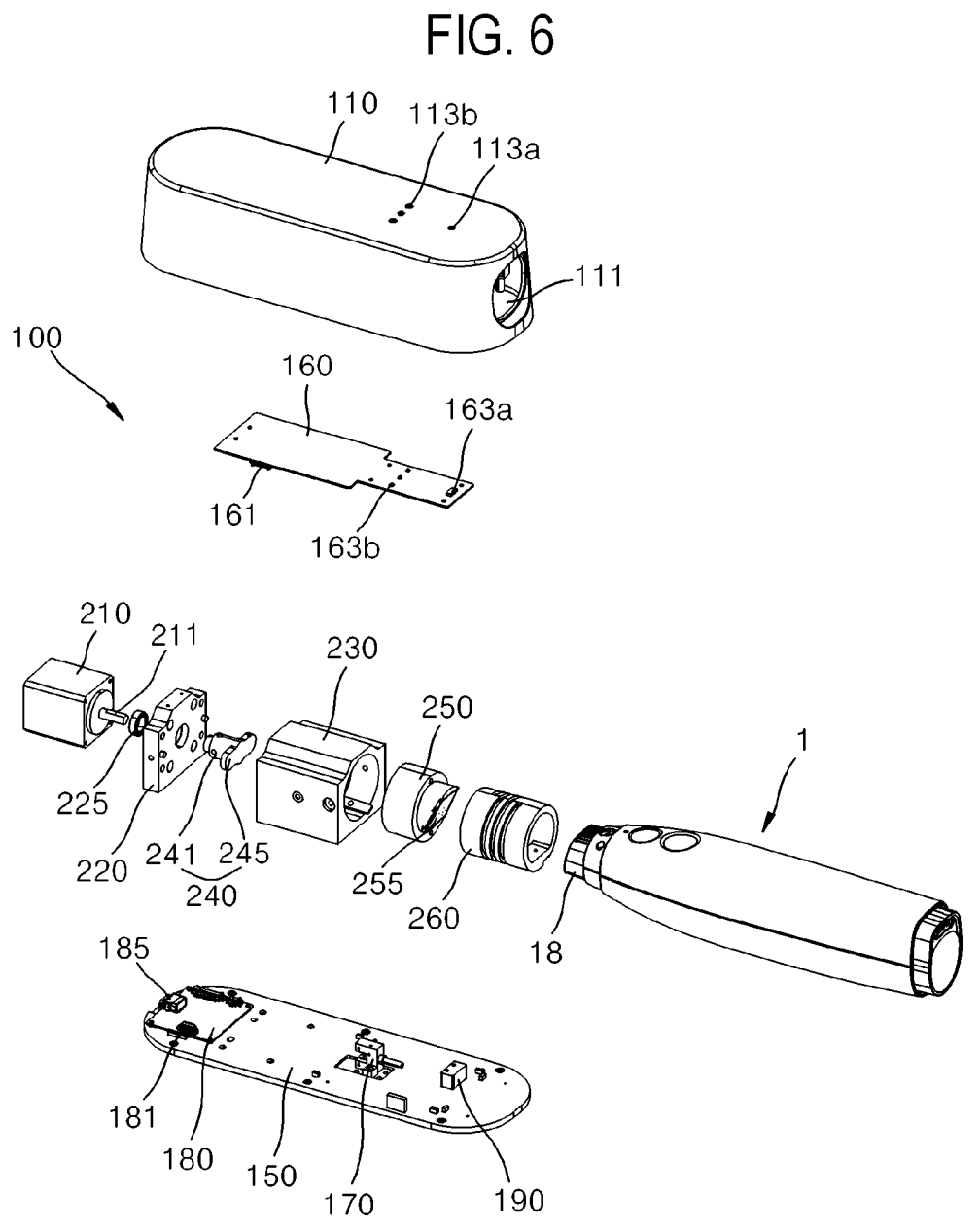
Figure 7:
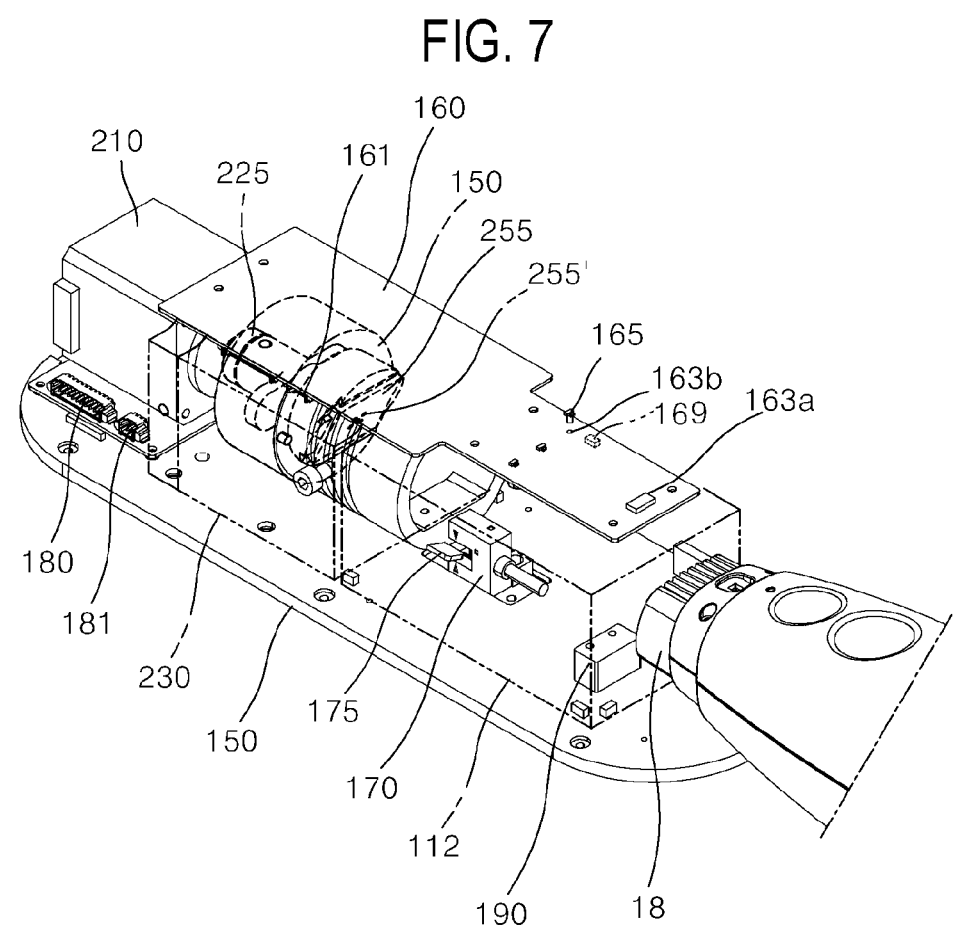

FIG. 3 is a use state diagram of an embodiment of a calibration cradle for a three-dimensional scanner according to the present disclosure. FIG. 4A and FIG. 4B are perspective views in one direction and in another direction of a calibration cradle for a three-dimensional scanner according to the present disclosure, respectively, in a state in which the three-dimensional scanner is disassembled from the configuration of FIG. 3. FIG. 5 and FIG. 6 are exploded perspective views of FIG. 4A and FIG. 4B, respectively. FIG. 7 is a projected perspective view showing the inside of the configuration of FIG. 3 in a state in which the cradle body is removed.

An embodiment of a calibration cradle 100 for a three-dimensional scanner according to the present disclosure relates to a calibration cradle 100 of a three-dimensional scanner 1 described with reference to FIG. 1 and FIG. 2. The above-described three-dimensional scanner 1 has been described as an oral scanner capable of scanning the patient's oral cavity as an example, but the three-dimensional scanner 1, which is calibrated via the calibration cradle 100 in the present embodiment, does not necessarily have to be an oral scanner, and may be applied to all known handheld scanners.

The three-dimensional scanner 1 according to an example may perform scanning via an optical member (see reference numeral 60 of FIG. 2) provided inside a tip case (see reference numeral 14 of FIG. 2). More specifically, the three-dimensional scanner 1 according to an example may have the optical member 60 on the tip case 14 inserted into the patient's oral cavity. The optical member is for easily scanning the inside of the narrow oral cavity of the patient. However, if a foreign substance such as moisture in the patient's mouth adheres to the optical member 60 when scanning the patient's oral cavity using the three-dimensional scanner 1, it may be impossible to perform accurate calibration. Therefore, in an embodiment of the calibration cradle 100 according to the present disclosure, in order to prevent negative effects of the optical member 60, calibration of the three-dimensional scanner 1 may be performed while the tip case 14 including the optical member 60 is separated from the three-dimensional scanner 1.

As referenced in FIGS. 3 to 7, an embodiment of the calibration cradle 100 according to the present disclosure may include a cradle body 110 having a scanner insertion hole 111 where the front end of the three-dimensional scanner 1 while the tip case 14 is removed is inserted and seated, a calibration pattern plate 255 (hereinafter, simply referred to as a "pattern plate") disposed inside the cradle body 110 to scanning-correct the three-dimensional scanner 1, and a pattern moving unit 200 for automatically moving the pattern plate 255 in at least one of axial rotation movement or axial movement inside the cradle body 110 when the three-dimensional scanner 1 is coupled to the cradle body 110. When the three-dimensional scanner 1 is inserted into the cradle body 110, the pattern plate 255 may be disposed to face the camera 20 provided inside the three-dimensional scanner 1. In addition, the axial direction in which the pattern plate 255 is moved may be defined as the longitudinal direction of the three-dimensional scanner 1 to be described later.

The lower surface of the cradle body 110 may be formed flat so as to be more stably supported and seated on a desk or a table where calibration is performed. In addition, the area of the lower surface of the cradle body 110 may be formed to be relatively larger than the area of the upper surface thereof, but is not limited thereto. The upper surface and the lower surface of the cradle body 110 may be formed to have rounded edges as a whole.

In addition, an irradiation path of outgoing light and incident light emitted from the light projector of the three-dimensional scanner 1 (see reference numeral 70 in FIG. 2) may be provided inside the cradle body 110, and particularly, the irradiation path of the outgoing light and the incident light may be provided in the form of a dark room to prevent the irradiation path from being affected by external light. When the front end of the three-dimensional scanner 1 is inserted into the scanner insertion hole 111, the inside of the cradle body 110 may form a dark room, and when the light projector 70 of the three-dimensional scanner 1 is operated to perform calibration, only the outgoing light emitted from the light projector 70 and the incident light in the form of reflected light reflected from the pattern plate 255 may exist inside the cradle body 110. Therefore, it is preferable that the scanner insertion hole 111 has a size which is capable of blocking external light from being introduced into the cradle body 110 when the three-dimensional scanner 1 is inserted.

Meanwhile, as referenced in FIG. 5, the cradle body 110 may include a main printed circuit board 150 configuring a lower surface thereof and shielding the inside of the cradle body 110 in a dark room form as described above.

In the main printed circuit board 150, elements such as a scanning position detection unit and a mounting sensor 190 to be described later may be mounted and arranged, and a feeding line (not shown) via which external power is supplied may be printed and formed. However, the lower surface of the cradle body 110 does not necessarily have to be provided in the same PCB form as the above-described main printed circuit board 150, and it is also possible to be provided in various other forms as long as power supply to each element 170 or 190 is possible.

In addition, although not shown in the drawings, a controller (not shown) for controlling the operation of a driving motor 210 among the elements of the pattern moving unit 200 to be described later may be mounted and disposed in the form of a MICOM on the main printed circuit board 150.

In addition, as referenced in FIG. 5, a motor PCB 180 for operation control and power supply of the driving motor 210 among the elements of the pattern moving unit 200 to be described later may be provided in the form of a sub-PCB inside the cradle body 110. An external power connector 185 capable of supplying external power by wired connection and an internal power connector 181 for power connection with a display PCB 160 to be described later may be mounted and arranged on the motor PCB 180.

In addition, as referenced in FIG. 5, the display PCB 160 for displaying an operation state of the calibration cradle 100 according to an embodiment of the present disclosure may be further included inside the cradle body 110.

The display PCB 160 may be disposed to be in close contact with an inner upper surface of the cradle body 110, a power on/off indicator lamp 163a and an operation state indicator lamp 163b may be provided in the form of an LED on an upper surface of the display PCB 160, and as described above, a power supply connector 161 for wired connection with the internal power connector 181 provided on one side of the motor PCB 180 may be provided on one side of the edge of the display PCB 160.

As referenced in FIGS. 5 to 7, a power on/off indicator hole 113a and an operation state indicator hole 113b through which light emitted from the power on/off indicator lamp 163a and the operation state indicator lamp 163b is transmitted to the outside may be formed on an upper surface of the cradle body 110.

As referenced in FIG. 7, the operation state indicator lamp 163b mounted and disposed on the display PCB 160 may emit light to the outside through the operation state indicator hole 113b via a light guide 165 made of a transparent material.

As referenced in FIGS. 4A, 4B, and 6, the scanner insertion hole 111 formed at one end of the cradle body 110 in the longitudinal direction may be formed in a shape in which the connection block 18 provided at the front end of the three-dimensional scanner 1 in a state where the tip case 14 is removed is capable of being inserted and seated. When the tip case 14 of the three-dimensional scanner 1 is removed, the connection block 18 may be exposed to protrude from the front end of the body case 10 by a predetermined length. The scanner insertion hole 111 may be formed in a shape where the connection block 18 protruding from the front end of the body case 10 is capable of being received therein.

In addition, although not shown in the drawings, an insertion configuration protrusion for configuring an insertion position of the connection block 18 may be formed to protrude from the scanner insertion hole 111. The insertion configuration protrusion may protrude in the form of a rib inside the scanner insertion hole 111 and may have any shape, and it is also possible to form a structure capable of preventing the connection block 18 of the three-dimensional scanner 1 from moving while being inserted into the scanner insertion hole 111.

An insertion configuration groove (not shown) configured to match the insertion configuration protrusion formed in the scanner insertion hole 111 may be formed at the front end of the body case 10 of the three-dimensional scanner 1 equipped with the connection block 18. More specifically, the insertion configuration groove may be formed on a lower side of the front end of the lower case 12 of the body case 10 of the three-dimensional scanner 1, but is not necessarily limited thereto.

The three-dimensional scanner 1 may be coupled to the calibration cradle while the insertion setting groove formed at the front end of the body case 10 and the insertion setting protrusion formed at the scanner insertion hole are mutually matched. Therefore, a user performing the calibration may identify the position of the insertion configuration groove provided in the three-dimensional scanner 1 and the insertion configuration protrusion formed in the calibration cradle 100 of the embodiment, and may couple the connection block 18 of the three-dimensional scanner 1 to the correct position.

In particular, the cradle body 110 of the calibration cradle 100 according to an embodiment of the present disclosure may be horizontally disposed on the upper surface of a desk or table prepared for performing calibration, and when the three-dimensional scanner 1 is moved in a horizontal direction and inserted into the scanner insertion hole 111 of the horizontally arranged cradle body 110, the lower surface of the three-dimensional scanner 1 may maintain a horizontal state while being supported by the upper surface of a desk or table.

To this end, when the three-dimensional scanner 1 is inserted into the scanner insertion hole 111, the scanner insertion hole 111 may be positioned on the same plane as the bottom of the three-dimensional scanner 1 and the bottom of the cradle body 110, and the three-dimensional scanner 1 and the cradle body 110 may be configured to a height capable of maintaining a horizontal state. In this way, as the lower end of the cradle body 110 and the lower end of the three-dimensional scanner 1 inserted and seated therein are located on the same plane, the three-dimensional scanner 1 may be supported horizontally so that the optical axis is stably maintained during the calibration process. Maintaining the optical axis via the stable leveling of the three-dimensional scanner 1 may improve the reliability of calibration.

As referenced in FIGS. 5 to 7, the mounting sensor 190 for detecting insertion and seating of the three-dimensional scanner 1 may be provided inside the cradle body 110.

When the connection block 18 of the three-dimensional scanner 1 inserted through the scanner insertion hole 111 is in contact with the mounting sensor 190, an electrical signal may be switched. To this end, it is preferable that the mounting sensor 190 is installed in a portion adjacent to the scanner insertion hole 111 in the inside of the cradle body 110. The mounting sensor 190 according to an example may be provided in the form of a tact switch, but is not necessarily limited thereto.

When the insertion and seating of the three-dimensional scanner 1 is detected via the mounting sensor 190, the controller may prepare the calibration cradle 100 for operation (stand-by), and may operate the power on/off indicator lamp 163a of the display PCB 160 to display the completion of the stable insertion and seating of the three-dimensional scanner 1 to the outside.

In addition, referring to FIG. 7, an illuminance sensor 169 for detecting predetermined light may be further provided inside the cradle body 110. When the three-dimensional scanner 1 is operated and predetermined light (e.g., "outgoing light") is emitted from the light projector 70 into the inner space of the cradle body 110, the illuminance sensor 169 may detect the light. The illuminance sensor 169 may detect the light, and may thus inform the controller of a time point at which the driving motor 210 is operable among the configuration of the pattern moving unit 200 to be described later.

More specifically, when the mounting sensor 190 detects that the front end of the three-dimensional scanner 1 is inserted and seated in the scanner insertion hole 111 of the cradle body 110, calibration may not be performed immediately, and if the illuminance sensor 169 recognizes that predetermined light is emitted from the light projector 70 due to the operation of the three-dimensional scanner 1, the pattern plate 255 may be restored to an initial position for calibration, thereby preparing for calibration.

The illuminance sensor 169 may be mounted on the lower surface of the display PCB 160 to more accurately measure the light in the inner space of the cradle body 110, but is not limited thereto.

In addition, as referenced in FIGS. 5 to 7, a scanning position detection unit configured to detect the position of the pattern plate 255 may be further provided inside the cradle body 110. The scanning position detection unit may detect the position of a mounting block 250 to which the pattern plate 255 is coupled, and may thus provide information so that the controller may calculate a required distance value and rotation angle value when calibration is performed. In addition, the scanning position detection unit may identify whether the pattern moving unit 200 is restored to an initial position when calibration is performed.

The scanning position detection unit performing this function may include, for example, a photo sensor unit and a hall sensor unit, but is not limited thereto.

For example, when the scanning position detection unit is the photo sensor unit, as referenced in FIG. 7, the photo sensor unit may include a photo sensor 170 fixed to the bottom surface of the cradle body 110 and a detection lead 175 which rotates and moves linearly by being coupled to the moving block 260 or the mounting block 250 to which the pattern plate 255 is coupled.

The detection lead 175 may be coupled to the front edge of the mounting block 250 or the moving block 260 among the elements of the pattern moving unit 200 to be described later, and may thus be interlocked and moved together when the mounting block 250 and the moving block 260 are axially rotated and/or linearly moved in an axial direction. When the detection lead 175 moves and is inserted between the photo sensor 170, the photo sensor 170 may detect the detection lead 175, may detect the positions of the moving block 260 and the mounting block 250 to which the detection lead 175 is coupled, and may detect the position of the pattern plate 255 coupled to the mounting block 250. The controller may obtain a separation distance and a rotation angle value between the pattern moving unit 200 or the pattern plate 255 and the photo sensor 170 via information acquired from the photo sensor unit.

As another example, when the scanning detection unit is a Hall sensor unit, although not shown in the drawings, the Hall sensor unit may include a Hall sensor (not shown) fixed to the cradle body 110 and a detection magnet (not shown) which is rotated and linearly moved in association with the pattern plate 255.

The detection magnet is an element which interacts with the Hall sensor via magnetism. The detection magnet may be provided on the front edge of the mounting block 250 or the moving block 260 among the elements of the pattern moving unit 200 to be described later, and when the mounting block 250 and the moving block 260 are axially rotated and/or linearly moved in an axial direction, the detection magnet may move in association with each other. When the detection magnet moves and is detected by the Hall sensor, the Hall sensor may detect the position of the detection magnet and may detect the position of the pattern plate 255 coupled to the mounting block 250. The controller may be configured to relatively measure a rotation angle value and a separation distance between the pattern moving unit 200 or the pattern plate 255 and the Hall sensor via information obtained from the Hall sensor unit.

When the three-dimensional scanner 1 is inserted and seated in the cradle body 110 and then the operation of the three-dimensional scanner 1 is detected via the illuminance sensor 169, the scanning position detection unit may identify the detected position of the pattern moving unit 200 (more specifically, the current position and rotation angle state of the pattern plate 255), and may present a reference value for restoring to the initial position if the position is not in the initial position for calibration.

The pattern moving unit 200 may be provided to move in a horizontal direction inside the cradle body 110 configured as described above. Hereinafter, "horizontal direction" may be defined as indicating a direction parallel to the upper surface of the table on which the cradle body 110 is mounted, and may be interpreted to include the longitudinal direction of the cradle body 110 and the longitudinal direction of the three-dimensional scanner 1.

The pattern moving unit 200 may be provided to be capable of axially rotating and reciprocating in the axial direction, which is the horizontal direction (i.e., the longitudinal direction of the cradle body 110) in which the front end of the three-dimensional scanner 1 is inserted and seated, and thus the pattern moving unit 200 may automatically move the pattern plate 255 to enable performing calibration. The pattern moving unit 200 may simultaneously axially rotate and axially move the pattern plate 255, and while the pattern plate 255 is moving, an angle between the pattern plate 255 and an optical axis of light emitted from the three-dimensional scanner 1 to the pattern plate 255 may be maintained.

The pattern moving unit 200 may be electrically operated by an external power source supplied via the above-described main printed circuit board 150 or an internal power source not shown but provided in the form of a rechargeable battery inside the cradle body 110. When an internal power source is provided as a rechargeable battery inside the cradle body 110, the rechargeable battery may be charged with power in a wired or wireless manner. A detailed description of the pattern moving unit 200 will be described later with reference to FIGS. 8, 9A, and 9B.

As referenced in FIG. 7, the pattern plate 255 may be printed or provided with a predetermined pattern 255' for calibration, and may be provided to perform calibration while being moved in association with the rotation or linear movement of the pattern moving unit 200.

As shown in FIG. 6, the pattern plate 255 may be disposed in an inclined manner on the front surface of the mounting block 250 to be described later. To this end, the front surface of the mounting block 250 may be inclined to have a predetermined inclination angle.

The inclination angle of the pattern plate 255 may be configured to be 40 degrees or more and less than 50 degrees based on the horizontal direction (the longitudinal direction of the three-dimensional scanner 1). This indicates that when the pattern plate 255 is orthogonal (i.e., 90 degrees) with reference to the horizontal direction, there is a disadvantage that each pattern 255' formed on the pattern plate 255 has the same depth information (or height information) on the same surface. Therefore, in an embodiment of the present disclosure, the pattern plate is designed to increase the calibration effect by disposing the pattern plate 255 to be inclined at a predetermined angle with respect to the horizontal direction.

Figure 8:
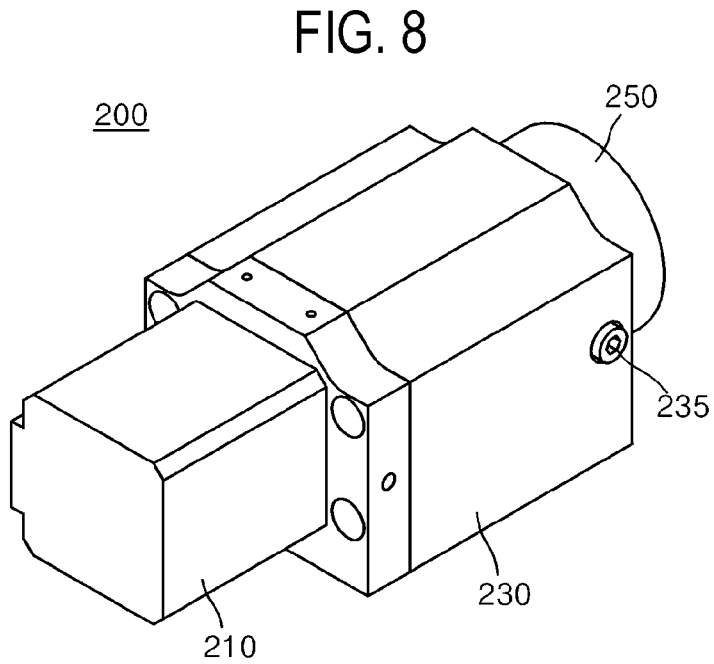
FIG. 8 is a perspective view showing a pattern moving unit of the configuration of FIG. 5.
Figure 9A:
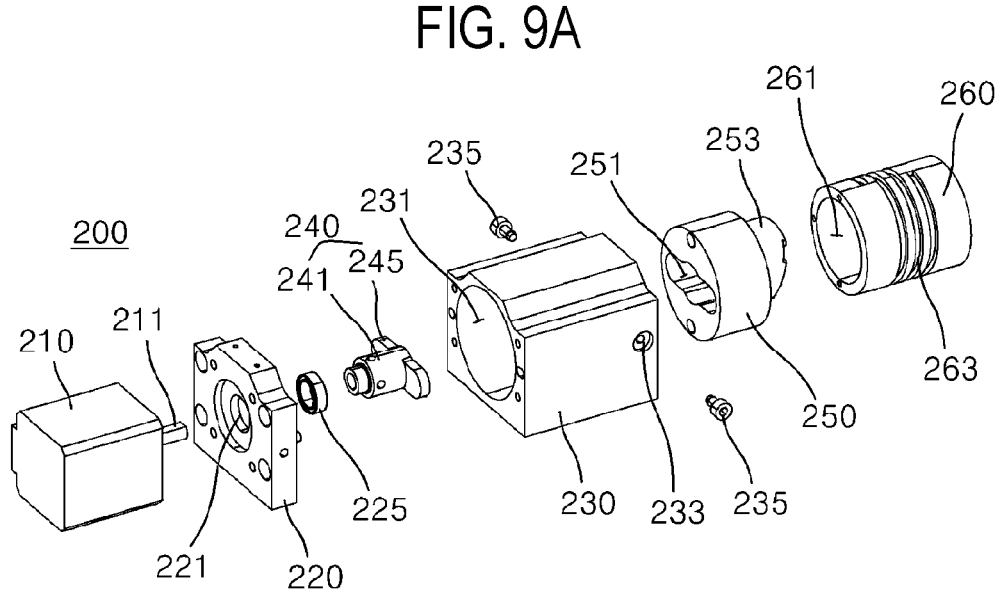
FIG. 9A and FIG. 9B are exploded perspective views showing the pattern moving unit of FIG. 8.
Figure 9B:
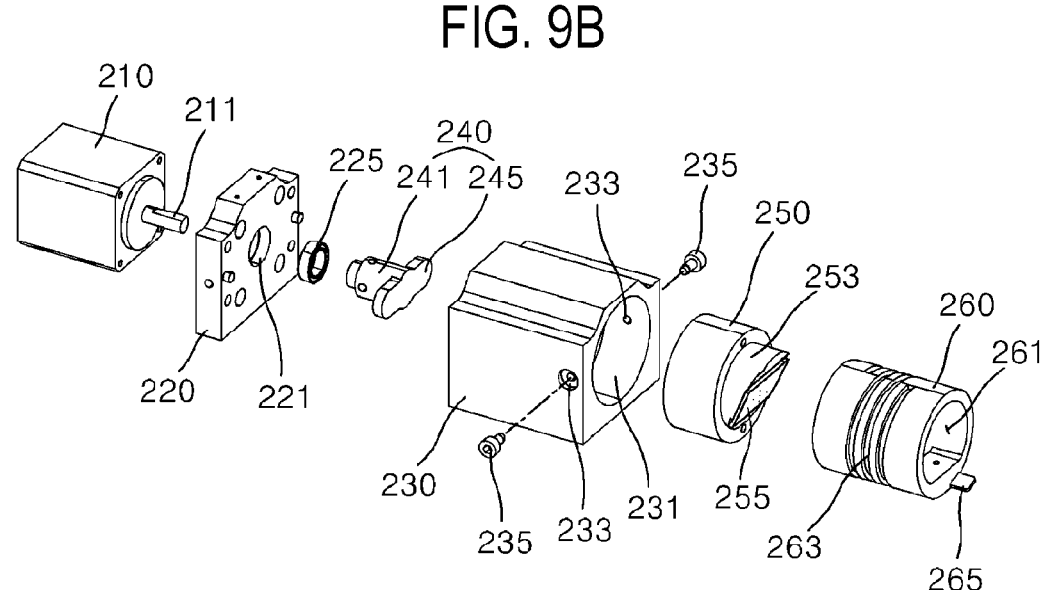
Figures 10A, 10B:
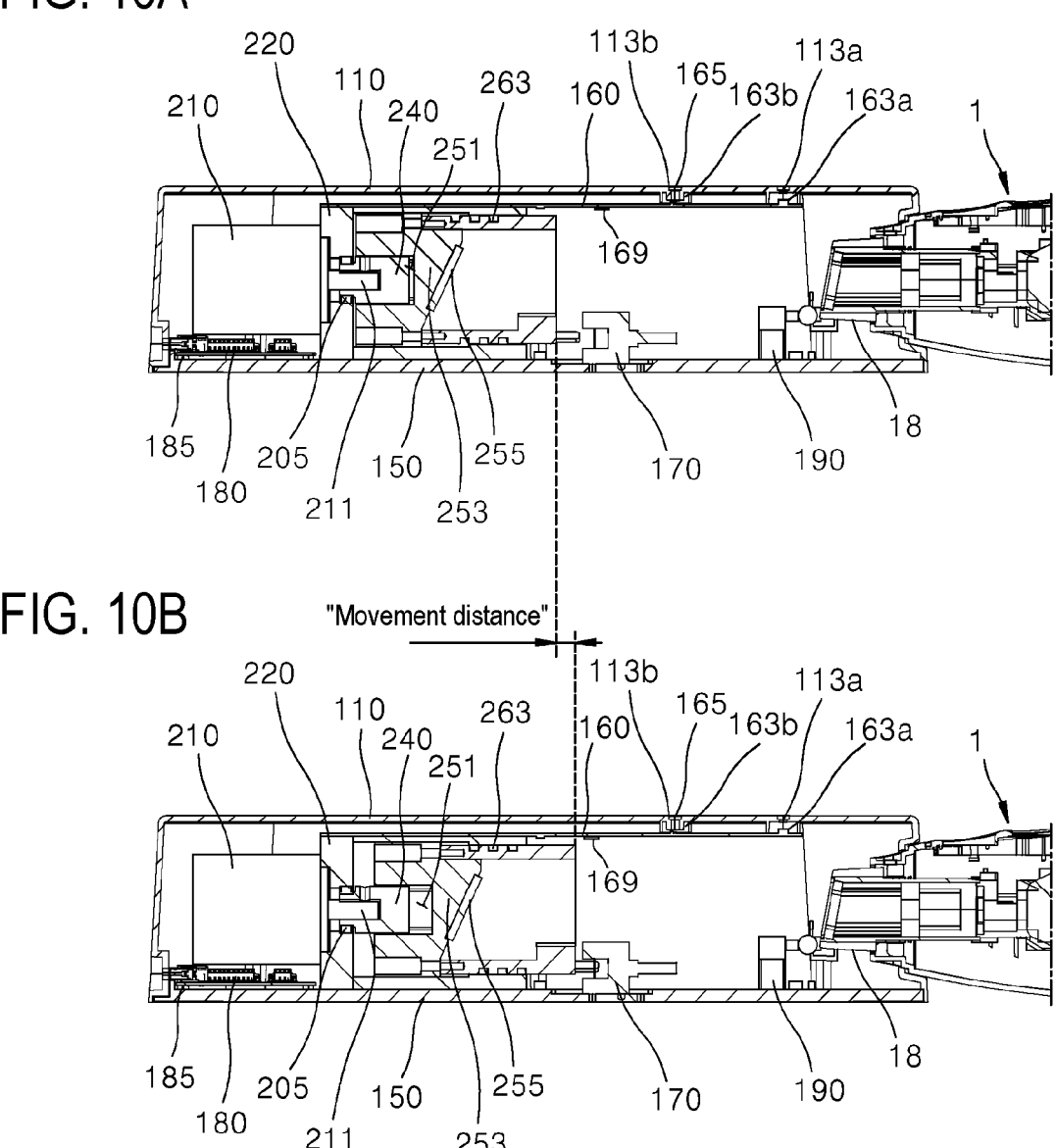
FIG. 10A and FIG. 10B are cross-sectional views showing the movement states of a pattern plate before and after operation of a calibration cradle for a three-dimensional scanner according to the present disclosure.
Figures 11A, 11B:
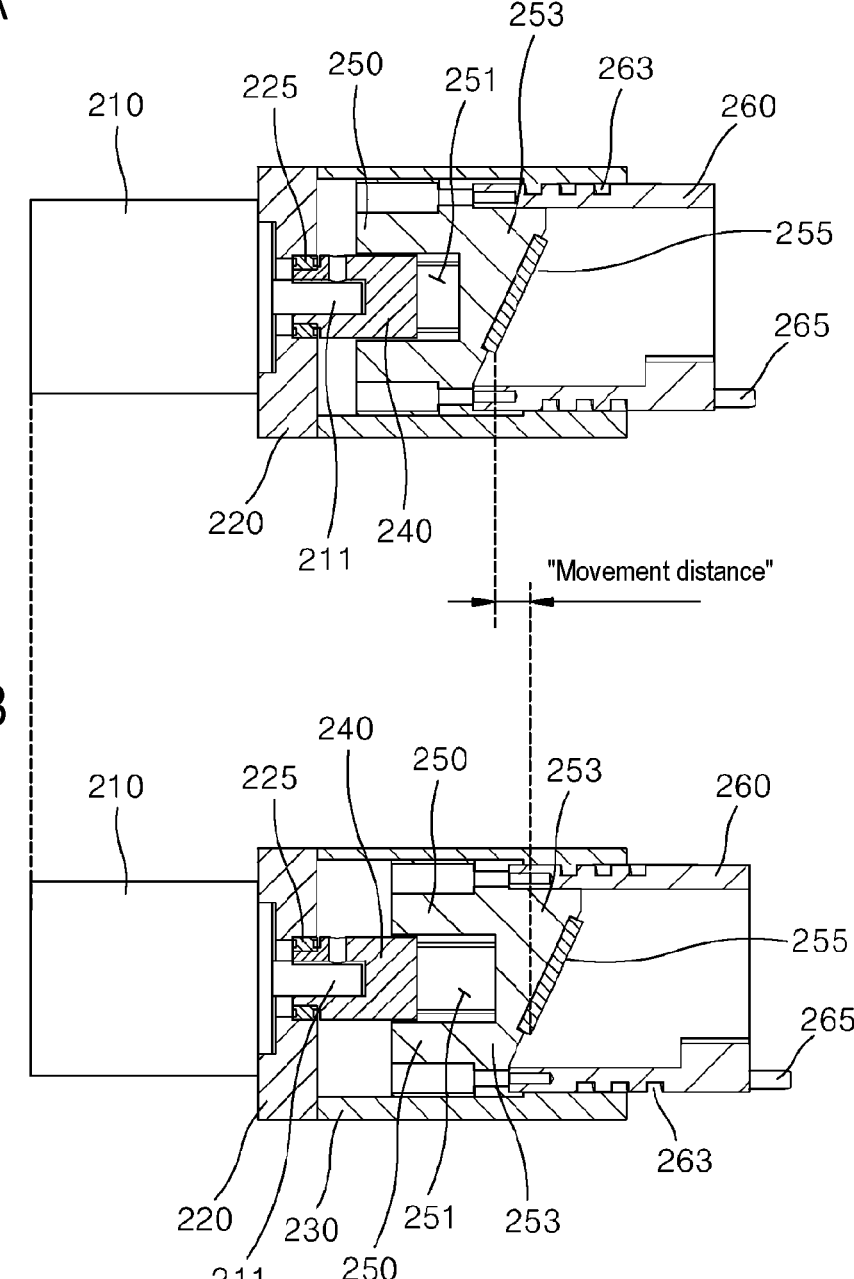
FIG. 11A and FIG. 11B are cross-sectional views showing the states before and after operation of the pattern moving unit of FIG. 8.
Figure 12A:
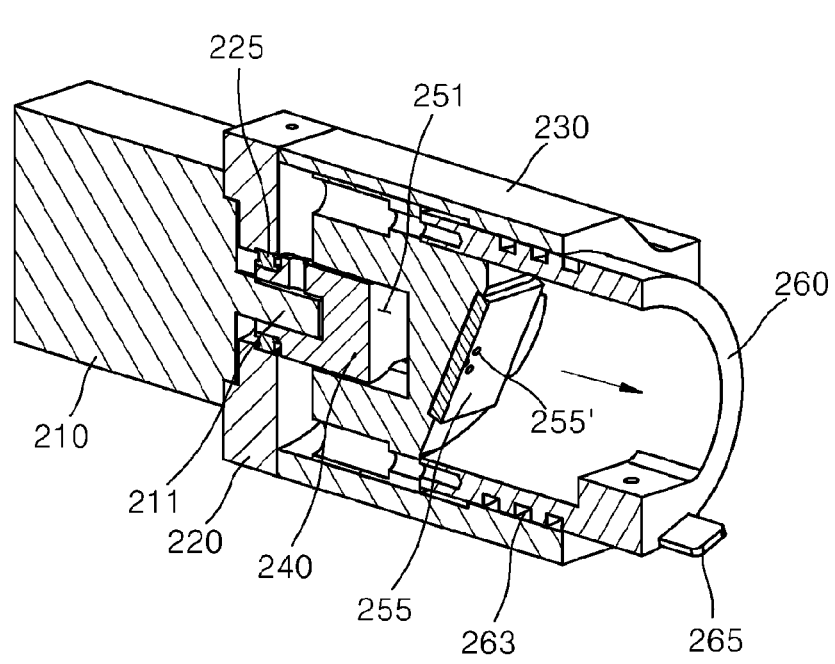
FIG. 12A and FIG. 12B are cross-sectional perspective views of the pattern moving unit of FIG. 11A and FIG. 11B.
Figure 12B:
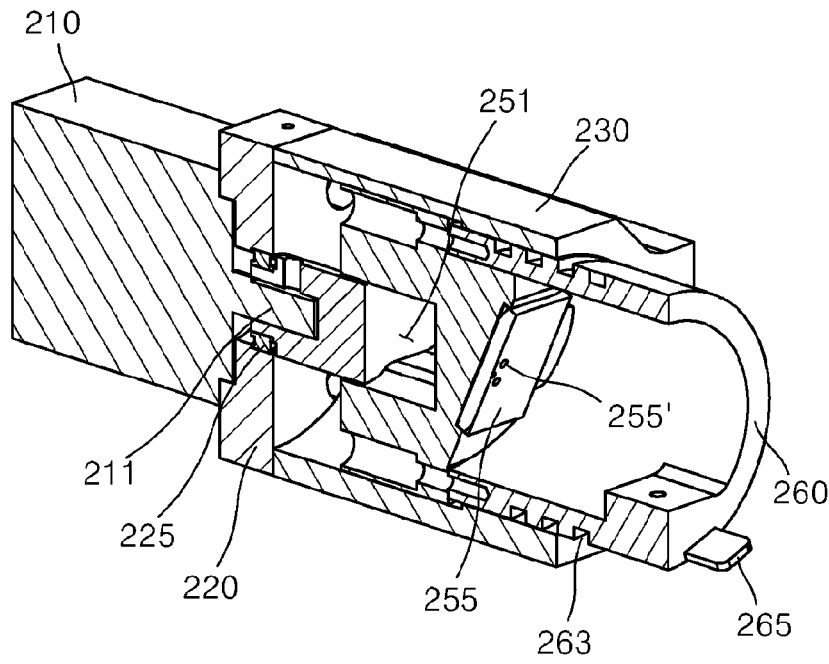

FIG. 8 is a perspective view showing a pattern moving unit of the configuration of FIG. 5. FIG. 9A and FIG. 9B are exploded perspective views showing the pattern moving unit of FIG. 8. FIG. 10A and FIG. 10B are cross-sectional views showing movement states of a pattern plate before and after operation of a calibration cradle for a three-dimensional scanner according to the present disclosure. FIG. 11A and FIG. 11B are cross-sectional views showing states before and after operation of the pattern moving unit of FIG. 8. FIG. 12A and FIG. 12B are cross-sectional perspective views of the pattern moving unit of FIG. 11A and FIG. 11B.

As referenced in FIG. 5, FIG. 6, and FIGS. 8 to 12, a pattern moving unit 200 may include a driving motor 210 electrically operated and having a rotary shaft 211, a fixing block 230 fixed inside the cradle body 110 and having a moving guide hole 231 which is open to one side and the other side thereof, and a mounting block 250 to which the pattern plate 255 is coupled and which is disposed in the moving guide hole 231 in the fixing block 230.

The driving motor 210 may be provided to be fixed adjacent to the other end side opposite to one end, through which the scanner insertion hole 111 is formed, of the inner space of the cradle body 110 and to allow the rotary shaft 211 to be parallel to or coincident with the optical axis. Therefore, it is natural that the axial direction of the pattern plate 255 moved by driving the driving motor 210 may be interpreted as coincident with or parallel to the optical axis of the light emitted from the three-dimensional scanner 1 to the pattern plate 255. The driving motor 210 as described above may be electrically driven using an external power source or an internal power source.

In addition, as shown in FIGS. 9A to 10B, the pattern moving unit 200 may include a transmission block 240 disposed between the driving motor 210 and the mounting block 250 to transmit the rotational force of the driving motor 210 to the mounting block 250.

The transmission block 240 may transmit the rotation force transmitted from the rotary shaft 211 of the driving motor 210 to the mounting block 250, and thus the mounting block 250 may rotate the pattern plate 255 disposed in an inclined manner on the inclined surface of a reception end 253 of the mounting block 250, which is formed an inclined manner, by being configured to be rotated in the moving guide hole 231 of the fixing block 230.

As referenced in FIG. 9 and FIG. 10, the transmission block 240 may include a coupling end 241 axially coupled to the rotary shaft 211 of the driving motor 210 and a rotation blade 245 provided at the front end of the coupling end 241 and inserted into a rotation interference hole 251 formed through the mounting block 250 to cause rotation interference.

When it is assumed that the coupling end 241 is formed to have a circular vertical cross section, the rotation blade 245 may be formed in a blade shape extending further to one side and/or the other side than the outer circumferential surface of the coupling end 241. When the transmission block 240 is rotated by the rotation blade 245 as described above, interference with the mounting block 250 may cause the mounting block 250 to rotate in association with the rotary shaft 211 of the driving motor 210.

The rotation interference hole 251 formed in the mounting block 250 and the rotation blade 245 of the transmission block 240 may have vertical cross sections corresponding to each other. In addition, the rotation interference hole 251 formed in the mounting block 250 may be formed in a shape which interferes with the rotation blade 245 in the rotational direction and does not interfere with the rotation blade 245 in the horizontal direction.

In this way, the rotation interference hole 251 may be formed to have a vertical cross section corresponding to the rotation blade 245 and may have a structure which does not interfere with each other in the horizontal direction (i.e., axial direction), and thus the mounting block 250 may be reciprocally moved in the axial direction by a moving block 260 to be described later.

In addition, it is preferable that the rotation interference hole 251 is formed such that a depth formed in the horizontal direction from the front end of the rotation blade 245 is at least greater than or equal to a horizontally movable distance of the mounting block 250. This is to prevent the movable distance of the pattern plate 255 from being limited by interference of the mounting block 250 and the transmission block 240, by forming the depth of the rotation interference hole 251 in the horizontal direction to be at least greater than the movable distance.

As referenced in FIG. 9, in the driving motor 210, the rotary shaft 211 may be stably supported via a center block 220 provided to be supported on the inner surface of the cradle body 110, and the transmission block 240 may be axially fixed to the front end of the rotary shaft 211 of the driving motor 210. The rotary shaft 211 of the driving motor 210 may be axially rotated and supported by a rotary bearing 225 interposed inside a through-hole 221 of the center block 220.

As referenced in FIG. 9, the pattern moving unit 200 may further include a moving block 260 provided to interlock with the mounting block 250 and linearly move the mounting block 250 in a horizontal direction by interference with the fixing block 230.

As referenced in FIGS. 9 to 12, the moving block 260 plays a role of reciprocating the pattern plate 255 in the horizontal direction (axial direction), while being rotated in association with the mounting block 250 to which the pattern plate 255 is coupled.

To this end, the moving block 260 may rotate and linearly move inside the moving guide hole 231, and a rotation guide groove 263 with which front ends of guide members 235 protruding into the moving guide hole 231 of the fixing block 230 are engaged may be formed on the outer circumferential surface of the moving block 260.

The rotation guide groove 263 may be formed on the outer circumferential surface of the moving block 260 and may be processed to be grooved in a spiral shape having a predetermined pitch interval so that the moving block 260 performs at least three rotations.

The guide members 235 may be provided in a pair to be spaced apart from each other at 180 degree intervals based on the center of the moving guide hole 231 of the fixing block 230, but the number and spacing are not limited thereto. One end of each of the guide members 235 may be inserted into the rotation guide groove 263 provided in a spiral shape.

The mounting block 250 may be provided to perform interlocking rotation with the moving block 260 and reciprocate linear movement in the horizontal direction, and the guide members 235 fixed to the fixing block 230 may be provided to be engaged with the rotation guide groove 263 formed on the outer circumferential surface of the moving block 260 which is rotated. Therefore, a linear movement distance of the pattern plate 255 may be determined according to a rotation amount of the moving block 260.

However, it is not necessary that the guide members 235 protrude into the fixing block 230 and the rotation guide groove 263 is provided on the outer circumferential surface of the moving block 260. That is, as described above, if the pattern plate 255 is capable of linear movement in the horizontal direction according to the rotation amount of the moving block 260, a structure opposite thereof may also be employed.

More specifically, although not shown in the drawings, a rotation guide groove with which guide members are engaged may be formed on an inner circumferential surface of the moving guide hole 231, and the guide members may be provided on an outer circumferential surface of the moving block 260.

In addition, the guide members 235 may be guide bolts which are partially inserted into the rotation guide groove 263. However, the guide members 235 may not necessarily be provided as guide bolts, and the guide members 235 may be ball plungers each having a bearing ball installed therein. When provided with a ball plunger, the guide member 235 has an advantage of minimizing frictional force due to rotation of the moving block 260.

Figure 13:
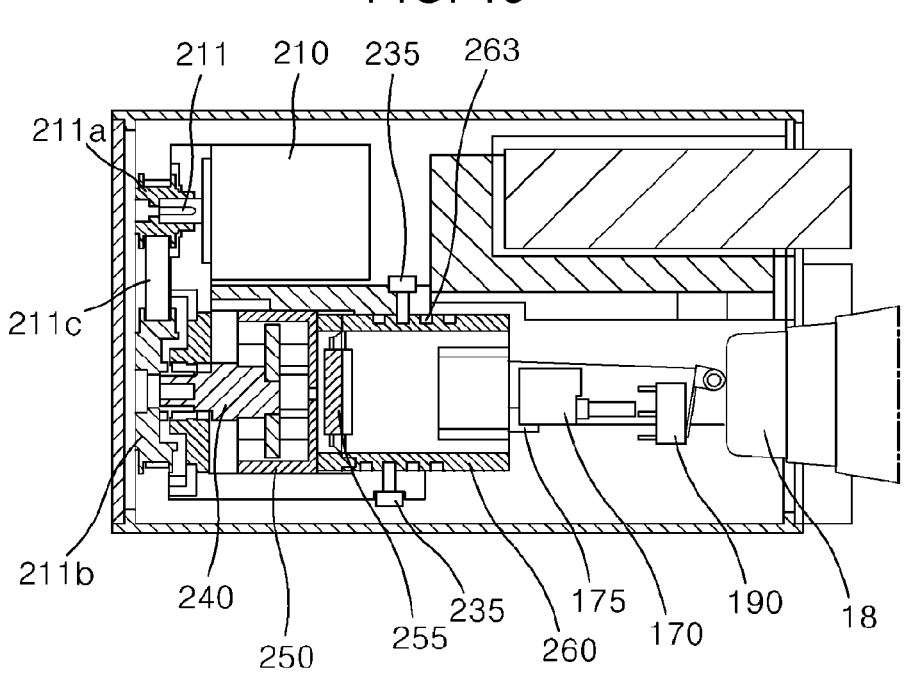
FIG. 13 is a cross-sectional view showing a calibration cradle for a three-dimensional scanner according to another embodiment of the present disclosure.
Figure 14:
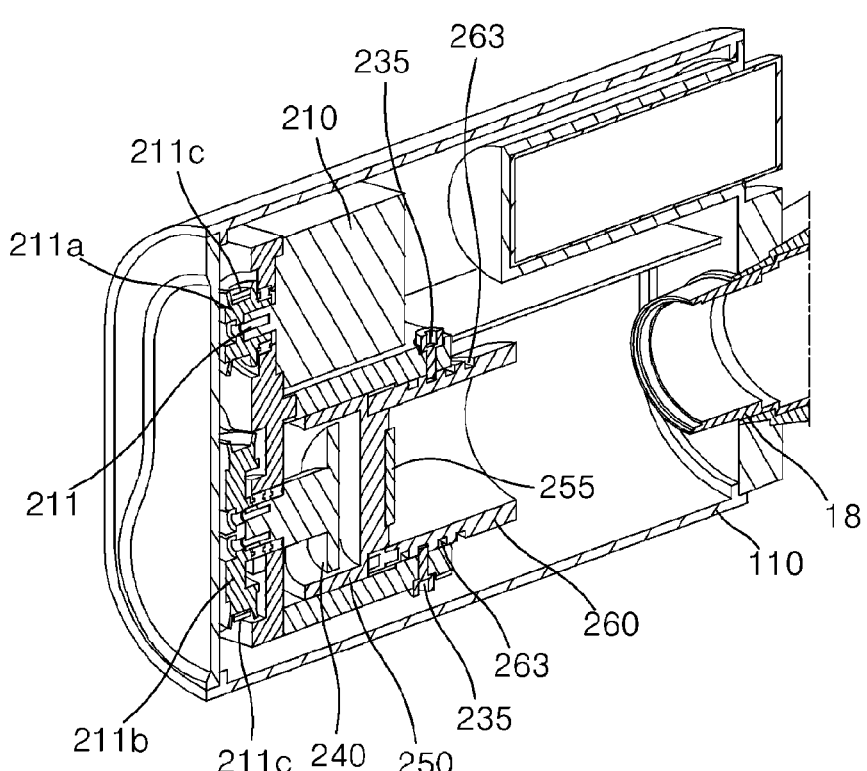
FIG. 14 is a cross-sectional perspective view of the calibration cradle of FIG. 13.

FIG. 13 is a cross-sectional view showing a calibration cradle for a three-dimensional scanner according to another embodiment of the present disclosure. FIG. 14 is a cross-sectional perspective view of the calibration cradle of FIG. 13.

A calibration cradle for a three-dimensional scanner according to an embodiment of the present disclosure described with reference to FIGS. 5 to 10 is provided such that the transmission block 240 is directly connected to the rotary shaft 211 of the driving motor 210 to have the same axis so as to directly transfer the rotational force of the driving motor 210 to the mounting block 250 via the transmission block 240.

However, the transmission block 240 does not necessarily need to be directly connected to the rotary shaft 211 of the driving motor 210. That is, as shown in FIGS. 13 and 14, it is also possible to transfer the rotational driving force of the driving motor 210 to the transmission block 240 in a belt driving transmission method.

More specifically, a driving belt pulley 211a may be provided to be directly connected to the rotary shaft 211 of the driving motor 210. The transmission block 240 may be disposed in parallel with the rotary shaft 211 of the driving motor 210 to be spaced apart from each other in the width direction of the cradle body 110, and may include a driven belt pulley 211b having the same axis at the front end of the transmission block. Rotational driving force of the driving motor 210 may be transmitted to via a transmission belt 211c wound around the driving belt pulley 211a and the driven belt pulley 211b.

An embodiment of a calibration control method for a three-dimensional scanner 1 using a calibration cradle 100 for a three-dimensional scanner according to the present disclosure configured as described above is briefly described as follows.

A control method for a calibration cradle for a three-dimensional scanner according to the present disclosure may include a scanner detection operation of detecting the insertion and seating of a three-dimensional scanner 1 into a cradle body 110 via a mounting sensor 190 provided inside a cradle body 110, a light detection operation of detecting, via an illuminance sensor 169, the light emitted by the operation of a light projector 70 of the three-dimensional scanner 1 after the three-dimensional scanner 1 is inserted into the cradle body 110, and a calibration performing operation of performing calibration by operating a pattern plate 255 which is linearly moved while rotating with reference to the optical axis inside the cradle body 110 when light is detected by the light detection operation.

More specifically, as referenced in FIGS. 10A to 12B, when the three-dimensional scanner 1 is inserted and seated in a scanner insertion hole 111 of the cradle body 110 in the horizontal direction, the insertion and seating of the three-dimensional scanner 1 may be detected by a mounting sensor 190 (the scanner detection operation) and the calibration cradle 100 according to an embodiment of the present disclosure may be switched to a preparation state (stand-by) for performing calibration.

Next, when the three-dimensional scanner 1 is operated and predetermined light emitted from the light projector 70 of the three-dimensional scanner 1 into the inner space of the cradle body 110 is identified via an illuminance sensor 169 (the light detection operation), operating power is applied to a driving motor 210, and when the position of the pattern plate 255 detected by the scanning position detection unit is not the initial calibration position, the driving motor 210 rotates and linearly moves a mounting block 250 and a moving block 260 to the initial positions.

When the pattern plate 255 is moved to the initial calibration position, the operation of the driving motor 210 may be controlled to perform calibration, and thus when a rotary shaft 211 of the driving motor 210 rotates in one direction, the mounting block 250 and the moving block 260 are interlocked and rotated via the transmission block 240, and by mutual engagement of the guide members 235 of the fixing block 230 and the rotation guide groove 263 of the moving block 260, the pattern plate 255 coupled to the mounting block 250 may be rotated and linearly moved in a horizontal direction (the calibration performing operation).

The driving motor 210 may be a stepping motor. The driving motor 210 may rotate by a predetermined amount each time there is a pulse. When the pattern plate 255 rotates by the amount predetermined by the driving motor 210 and then stops, the camera 20 of the three-dimensional scanner 1 may operate to obtain calibration data. The rotation and stop operation of the pattern plate 255 may be repeated several times (for example, a total of 9 times) from the initial position for calibration to the final position, and the camera 20 of the three-dimensional scanner 1 may also be operated repeatedly several times (for example, a total of 9 times) to obtain calibration data.

In addition, an embodiment of the calibration cradle of the present disclosure may obtain information about the position and rotation angle of the pattern plate 255 using a scanning position detection unit, and may obtain continuous result values (data) of multiple points using a controller, thereby providing an advantage of performing more accurate and reliable calibration. Calibration may be performed based on data of multiple points acquired during a single calibration process in which the pattern plate 255 is operated from the initial position and rotated and linearly moved to the final position, thereby providing an advantage of greatly reducing the time required for the calibration process.

Figure 15:
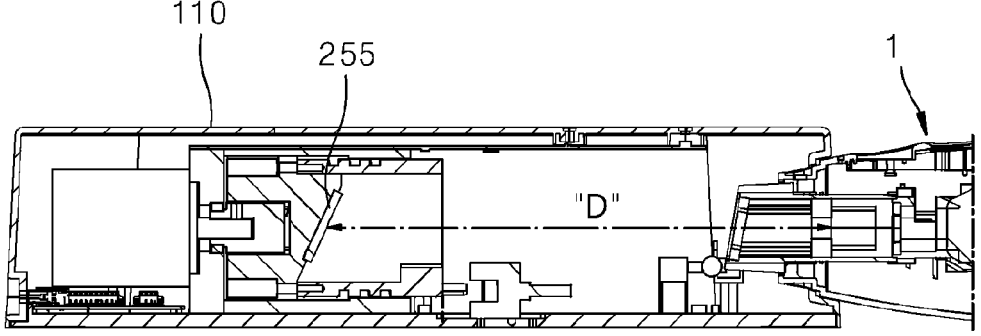
FIG. 15 illustrates a perspective view and a cross-sectional view showing an example of a linear reciprocating movement design of a calibration cradle for a three-dimensional scanner according to an embodiment of the present disclosure.

FIG. 15 illustrates a perspective view and a cross-sectional view showing an example of a linear reciprocating movement design of a calibration cradle for a three-dimensional scanner according to an embodiment of the present disclosure.

As described above, in the three-dimensional scanner 1, which performs calibration using a calibration cradle for a three-dimensional scanner according to an embodiment of the present disclosure, while the tip case 14 is removed, the front end of the body case 10 is inserted into the scanner insertion hole 111, and then calibration is performed. The tip case 14 may be manufactured in various specifications having various lengths, and it is desirable to configure the initial position of the pattern plate 255 differently for performing calibration. That is, when the three-dimensional scanner is inserted into the cradle body 110 while the tip case 14 provided in the three-dimensional scanner 1 is removed, considering that the tip case 14 is manufactured in various specifications having various lengths, an initial position of the pattern plate 255 for performing calibration may be differently configured according to a distance between the camera 20 and the optical member 60 in the tip case 14.

More specifically, referring to the upper drawing of FIG. 15, a distance between the camera 20 and the optical member 60 in the tip case 14 may be defined as "A," and a distance between the optical member 60 and an object to be measured may be defined as "B." A scan error distance (C) may be configured based on the distance (B) between the optical member 60 and the object to be measured.

Therefore, at the time of performing calibration using a calibration cradle for a three-dimensional scanner according to an embodiment of the present disclosure, it is desirable to configure a distance (D) between the camera 20 and the pattern plate 255 within the range of the sum of the distance (B) between the optical member 60 and the object to be measured and a half (C/2) of the scan error distance, while including the distance (A) between the camera 20 and the optical member 60. In other words, the distance (D) between the camera 20 and the pattern plate 255 may be as small as the distance (A) between the camera 20 and the optical member 60, and may be as great as the sum of the distance (A) between the camera 20 and the optical member 60, the distance (B) between the optical member 60 and the object to be measured, and the half (C/2) of the scan error distance. Therefore, at the time of performing calibration, the initial and final positions of the pattern plate 255 may be configured in consideration of the minimum distance and the maximum distance. In addition, a movement area of the pattern plate 255 for performing calibration may be between the initial position and the final position.

As described above, it is necessary to configure the initial position of the pattern plate 255 for performing calibration to be different depending on the distance (A) between the camera 20 and the optical member 60 of the tip case 14 provided in various specifications.

For example, assuming that a first tip case 14 having a length of the distance (A) of 95 mm and a second tip case 14 having a length of the distance (A) of 100 mm are manufactured, both the three-dimensional scanner 1 to which the first tip case 14 is applied and the three-dimensional scanner 1 to which the second tip case 14 is applied may be calibrated using the calibration cradle of the present disclosure. In order to perform calibration of the three-dimensional scanner 1 to which the first tip case 14 is applied, the initial position of the pattern plate 255 may be configured such that the distance between the pattern plate 255 and the camera 20 in the case of applying the first tip case 14 is closer than the distance between the pattern plate 255 and the camera 20 in the case of applying the second tip case 14.

Conversely, in order to perform calibration of the three-dimensional scanner 1 applying the second tip case 14, the initial position of the pattern plate may be configured such that the distance between the pattern plate 255 and the camera 20 in the case of applying the second tip case 14 is farther than the distance between the pattern plate 255 and the camera 20 in the case of applying the first tip case 14.

In the above, an embodiment of a calibration cradle for a three-dimensional scanner according to the present disclosure has been described in detail with reference to the accompanying drawings. However, the embodiments of the present disclosure are not necessarily limited to the above-described embodiments, and it will be understood for granted that various modifications and implementations within an equivalent scope are possible by those skilled in the art in the technical field to which the present disclosure belongs. Therefore, it will be noted that the true scope of the present disclosure is determined by the claims described later.

INDUSTRIAL APPLICABILITY

The present disclosure provides a calibration cradle for a three-dimensional scanner and a control method therefor, wherein in order to perform more accurate calibration of the three-dimensional scanner and improve user convenience, the pattern plate is automatically moved when the three-dimensional scanner is inserted and seated in the calibration cradle.

What is claimed is:

1. A calibration cradle for a three-dimensional scanner, the calibration cradle comprising:
   a cradle body into which at least a part of the three-dimensional scanner including a camera is inserted;
   a pattern plate disposed inside the cradle body to face the camera to calibrate the three-dimensional scanner; and
   a pattern moving unit configured to automatically move the pattern plate by at least one of axial rotation movement around an axis or axial movement along the axis when the three-dimensional scanner is coupled to the cradle body,
   wherein a direction of the axis is a longitudinal direction of the three-dimensional scanner.

2. The calibration cradle of claim 1, wherein the axis coincides with or is parallel to an optical axis of light emitted from the three-dimensional scanner to the pattern plate.

3. The calibration cradle of claim 1, wherein the pattern moving unit causes the pattern plate to make axial rotation movement and axial movement at the same time, and
   wherein, while the pattern plate moves, an angle between the pattern plate and the optical axis of light emitted from the three-dimensional scanner to the pattern plate is maintained.

4. The calibration cradle of claim 1, wherein a scanner insertion hole into which the three-dimensional scanner is inserted is formed in the cradle body, and
   wherein the scanner insertion hole is configured to be at a height at which the bottom of the three-dimensional scanner inserted horizontally and the bottom of the cradle body are coplanar.

5. The calibration cradle of claim 1, wherein a scanner insertion hole into which the three-dimensional scanner is inserted is formed through the cradle body, and
   wherein the scanner insertion hole has a size such that external light is blocked from being introduced into the cradle body when the three-dimensional scanner has been inserted into the scanner insertion hole.

6. The calibration cradle of claim 1, wherein the pattern moving unit is electrically operated by an internal power source charged wirelessly or by wire.

7. The calibration cradle of claim 1, wherein the cradle body comprises at least one of:
   a mounting sensor configured to detect insertion and seating of the three-dimensional scanner; or
   a scanning position detection unit configured to detect the position of the pattern plate.

8. The calibration cradle of claim 1, wherein an illuminance sensor configured to detect light is provided inside the cradle body, and
   wherein the illuminance sensor detects light emitted from the three-dimensional scanner to the pattern plate.

9. The calibration cradle of claim 1, wherein the pattern moving unit comprises:
   a driving motor electrically operated and having a rotary shaft;
   a fixing block fixed inside the cradle body and having a horizontally opened moving guide hole formed therein; and
   a mounting block having the pattern plate coupled thereto and disposed in the moving guide hole inside the fixing block, and
   wherein the axial direction of the axial rotation movement or the axial movement is an axial direction of the rotary shaft.

10. The calibration cradle of claim 9, wherein the pattern moving unit further comprises a transmission block disposed between the driving motor and the mounting block to transmit rotational force of the driving motor to the mounting block, and
   wherein the transmission block comprises:
   a coupling end coupled to the rotary shaft of the driving motor; and
   a rotation blade provided at the coupling end and inserted into a rotation interference hole formed in the mounting block to cause rotation interference.

11. The calibration cradle of claim 10, wherein the rotation interference hole formed in the mounting block is formed in a shape which interferes in the rotational direction of the rotation blade and does not interfere in the horizontal direction of the rotation blade.

12. The calibration cradle of claim 10, wherein the rotation interference hole is formed such that a depth formed in a horizontal direction from the rotation blade is greater than or equal to a horizontally movable distance of the mounting block.

13. The calibration cradle of claim 10, wherein the transmission block receives the rotational driving force of the driving motor via a transmission belt wound around a driving belt pulley provided on the rotary shaft of the driving motor and a driven belt pulley disposed parallel to the rotary shaft of the driving motor.

14. The calibration cradle of claim 9, wherein the pattern moving unit further comprises a moving block provided to interlock with the mounting block and configured to move the mounting block by at least one of rotational movement or linear movement by interference with the fixing block.

15. The calibration cradle of claim 14, wherein the moving block moves within the moving guide hole, and a rotation guide groove in which a guide member is engaged is formed on an outer circumferential surface of the moving block or an inner circumferential surface of the fixed block.

16. The calibration cradle of claim 1, wherein the three-dimensional scanner comprises a light projector, and
wherein light emitted from the light projector is irradiated directly to the pattern plate without going through another element.

17. The calibration cradle of claim 1, wherein, when the pattern plate is moved at least once, the camera is operated at least once.

18. The calibration cradle of claim 1, wherein, when the three-dimensional scanner is inserted into the cradle body while the tip case provided in the three-dimensional scanner is removed, the initial position of the pattern plate for performing calibration is configured differently according to the distance between the camera and the optical member in the tip case.

19. A control method for a calibration cradle for a three-dimensional scanner, the control method comprising:
a scanner detection operation of detecting the insertion of the three-dimensional scanner into a cradle body;
a light detection operation of detecting light emitted by an operation of the three-dimensional scanner; and
a calibration performing operation of performing calibration by automatically moving a pattern plate inside the cradle body by at least one of axial rotation movement around an axis or axial movement along the axis when light is detected by the light detection operation,
wherein, during the calibration performing operation, the position information of the pattern plate is provided to a controller via a scanning position detection unit provided inside the cradle body, and
wherein a direction of the axis is a longitudinal direction of the three-dimensional scanner.

20. The control method of claim 19, wherein, in the calibration performing operation, when light is detected by the light detection operation after the three-dimensional scanner is inserted, the pattern plate is restored to an initial position for performing the calibration.

* * * * *